United States Patent [19]

Biondo et al.

[11] 4,142,629
[45] Mar. 6, 1979

[54] DISPOSABLE DENTAL CAPSULE

[75] Inventors: Joseph G. Biondo, Watchung; Salvatore L. Savarese, Warren, both of N.J.

[73] Assignee: Engelhard Minerals & Chemicals Corporation, Iselin, N.J.

[21] Appl. No.: 857,340

[22] Filed: Dec. 5, 1977

[51] Int. Cl.² ............................................. B65D 81/32
[52] U.S. Cl. ............................. 206/219; 215/DIG. 8; 206/220
[58] Field of Search .............. 206/219, 220, 221, 63.5; 215/DIG. 8

[56] References Cited
U.S. PATENT DOCUMENTS

| 3,139,180 | 6/1964 | Kobernick | 206/221 |
| 3,917,062 | 11/1975 | Winters | 206/219 |

Primary Examiner—William T. Dixson, Jr.
Attorney, Agent, or Firm—R. Jonathan Peters; Victor E. Libert

[57] ABSTRACT

A small two-part capsule for receiving and for storing separately individual ingredients and for mixing them together has two cavities in one part which receive the ingredients separately. The cavities are sealed by the other part via a screw thread connection. When the capsule is inverted and the connection is loosened, the ingredients from one cavity flows into the other. Novel sealing means is provided between the two parts.

9 Claims, 7 Drawing Figures

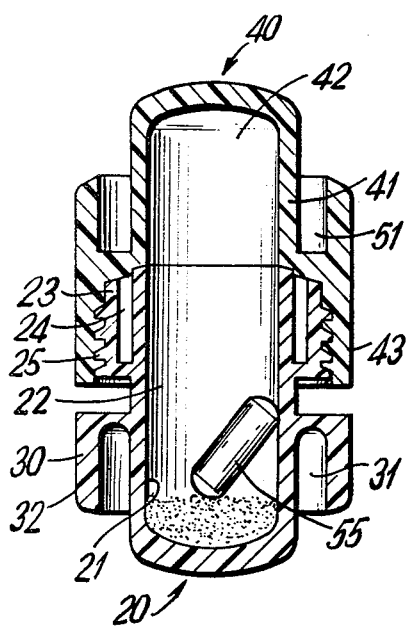
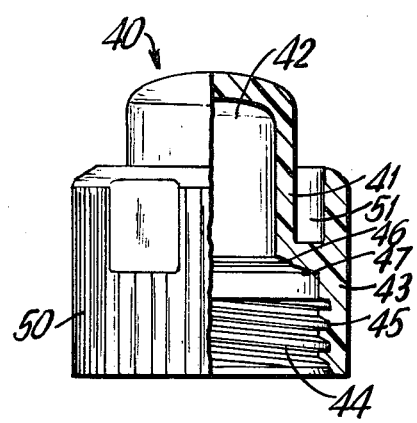
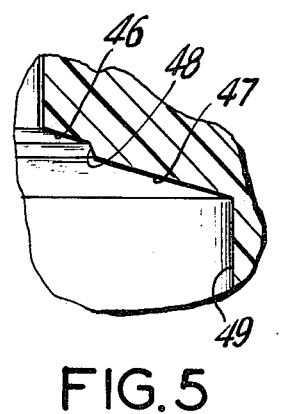
FIG. 3   FIG. 1   FIG. 5
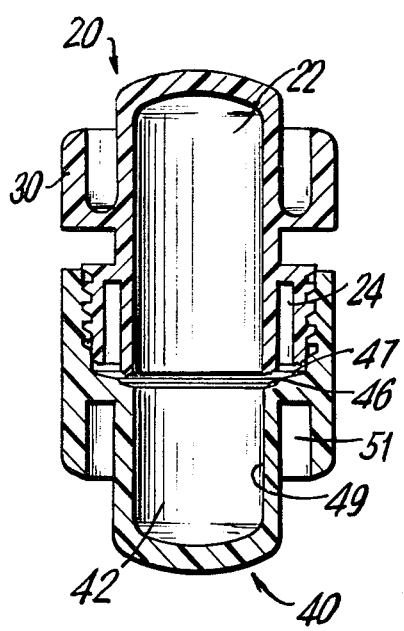
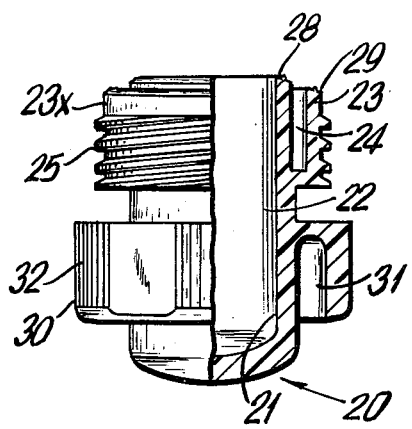
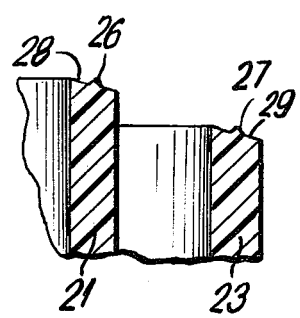
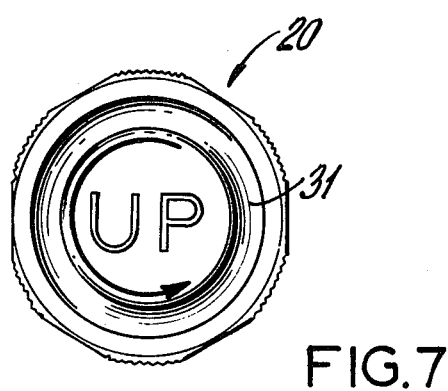
FIG. 4   FIG. 2   FIG. 6   FIG. 7

DISPOSABLE DENTAL CAPSULE

BACKGROUND OF THE INVENTION

This invention relates to containers or capsules for receiving, storing, shipping and mixing ingredients which must be kept separate until needed for use.

The invention is particularly useful in the making of dental amalgams by mixing mercury and silver alloy powders. These ingredients require careful measurement and mixing and they must be kept separate until just before use.

Because of the need for delicate measuring apparatus and the time consuming operation of measuring and mixing by dentists, the art has developed a number of capsule constructions. In them the mercury and the silver powders, in bulk or tablet form were kept in separate compartments until just before the amalgam was to be prepared and used. These prior constructions required three or more parts, including two container bodies and a screen, or a valve, which required rotation or sliding of the container parts until the valve ports came into register.

One of the problems in the prior art was keeping the mercury from leaking during the mixing and trituration of the ingredients. This led some workers to use three container parts, thus adding to the cost of manufacture due to the need for three dies or molds and more molding material.

It is an object of this invention to provide a capsule or container having only two cooperating parts which when held tightly together hermetically seal two ingredients in two separate cavities and which when loosened and inverted permit direct flow of one ingredient into a chamber for mixing with the other ingredient.

Other objects and advantages will appear as the invention is described in connection with the drawing.

According to the invention, a container consisting of two parts which are connected by a screw threaded connection and each container part has a cylindrical cavity, which together provide a chamber wherein two ingredients are mixed. One container part has an annular cavity in which one ingredient is contained while a second ingredient is contained in the aforementioned cavity of that part. Sealing means preferably in the form of concentric annular ribs are provided on the edges of the cavities engage with shoulder means on the other container part so that when the parts are screwed tight the ingredients are maintained separately and out of contact with one another but when the sealing engagement of the ribs and shoulder means is loosened and the container is inverted, the two ingredients can flow together in the mixing chamber and mixed by shaking the container. The connection of the two container parts is tightend before the shaking.

In accordance with the present invention, there is provided a container for storing and mixing ingredients consisting of a first part having an inner, first wall and an outer, second wall. The first wall has a circumferential first wall edge on which first annular sealing means are formed, the first wall defining an inner cavity open at one end and adapted to hold a first ingredient. The second wall has a second wall edge on which second annular sealing means are formed, the second wall being disposed circumferentially outwardly of the first wall and joined thereto to define an annular cavity disposed outwardly of the first wall edge and open at one end. The annular cavity is adapted to hold a second ingredient, the open ends of the first and annular cavities facing the same direction and the second sealing means are disposed concentrically outwardly of the first sealing means. A second part having a second part wall defining a second cavity open at one end is also provided, the second part further having an annular shoulder means formed thereon. Respective cooperating interengageable means are formed, respectively, on the first and second parts and are adapted to cooperate with each other to engage the first and second parts with each other whereby the first and second cavities cooperate to form a mixing chamber and the first and second sealing means firmly engage the annular shoulder means to seal the annular cavity and the mixing chamber both from each other and from exteriorly of the container. The interengageable means are releasable by relative rotational movement of the first and second parts to a selected extent whereby the first and second parts are axially moved relative to each other to separate the first sealing means from the annular shoulder means sufficiently to provide a flow path over the entire periphery of the shoulder means from the annular cavity to the mixing chamber while maintaining both sealed from exteriorly of the container, so that upon inverting of the container the second ingredient in the annular cavity may flow into said mixing chamber for mixing of said ingredients.

In accordance with one aspect of the invention, the container further includes an inclined portion on the second container part adjacent the annular shoulder means and positioned and configured to sealingly engage the first wall adjacent the first wall edge when the first and second parts are engaged by the interengageable means to provide a second inner seal which cooperates with the first sealing means to provide a double seal between the mixing chamber and the annular cavity.

In accordance with another aspect of the invention, the container further includes a circumferentially extending surface on the first part adjacent the second wall edge thereof, this circumferentially extending surface being positioned and configured to sealingly engage the second part when the first and second parts are engaged by the interengageable means to provide a second outer seal which cooperates with the second sealing means to provide a double seal between the annular cavity and exteriorly of said container.

Certain other aspects of the invention provide the interengageable means in the form of mating interior and exterior screw threads and the sealing means in the form of ribs, preferably in the form of ribs formed with substantially straight converging sides meeting at approximately a 90° angle.

BRIEF DESCRIPTION OF THE DRAWINGS

In the drawings:

FIG. 1 is a side elevation view partly in axial mid-section of one part of a container embodying the invention.

FIG. 2 is a side elevation view partly in axial mid-section of the second part of a container embodying the invention.

FIG. 3 is a longitudinal or axial cross-section view of the parts in FIGS. 1 and 2 when firmly engaged.

FIG. 4 is a view similar to FIG. 3 but with the parts loosely engaged and inverted.

FIG. 5 is an enlarged detail section view broken away from FIG. 1 showing the shoulder portion of the sealing means.

FIG. 6 is an enlarged detail section view broken away from FIG. 2 showing the rib portion of the sealing means.

FIG. 7 is a plan view of the container looking at the end of the part shown in FIG. 2.

DESCRIPTION OF THE PREFERRED EMBODIMENTS

Referring to the drawings and particularly to FIGS. 2 and 3, a first container part 20 is formed to receive two ingredients. The form of invention illustrated is particularly designed for use by dentists in the mixing of mercury and silver alloy powders to form an amalgam for filling teeth. The amounts of mercury and silver alloy powders are pre-measured in desired amounts and are deposited in one container part, 20, when it is positioned upright as illustrated in FIGS. 2 and 3. It is necessary that the ingredients be kept apart until they are to be mixed and used. For that purpose the part 20, which for convenience will be called the receptacle, is formed with a cylindrical wall 21 which is closed at its bottom end providing an upwardly open cavity 22 (referring to FIG. 2), to receive the measured amount of silver powder. Concentrically around the upper end of wall 21 a cylindrical outer wall 23 is formed joined at its lower end to wall 21, thereby providing an upwardly open annular cavity 24 to receive the measured amount of mercury.

The outer surface of wall 23 is provided with an external screw thread for engagement with an internal screw thread on the other part of the receptacle as will presently be described.

In order to close the cavities 22 and 24, a cap part 40 is provided as illustrated individually in FIG. 1. The cap is formed with a cylindrical wall 41 providing a cavity 42 of equal diameter to receptacle cavity 22 whereby the two cavities 22, 42 form a mixing chamber when the cap and receptacle parts are secured together. The lower or open end of the cap (referring to its position in FIG. 1) is enlarged forming an enlarged cylindrical mouth 44. An internal screw thread 45 is formed on the inner periphery of mouth 44 to mate with the threads 25 on the receptacle when the receptacle is inserted into mouth 44 and rotated to secure the cap and receptacle parts together.

In order to provide a tight seal when the cap and receptacle are secured together an annular rib 26 is formed on the edge 28 of the wall 21 and a similar annular rib 27 is formed on the edge 29 of the wall 23. Preferably these ribs each project from said edges with straight sides converging to a peak at an approximately 90° angle. It is within the scope of the invention, however, for the ribs to have a curved or other cross-sectional profile.

The peaks of the ribs 26, 27 engage, respectively, flat shoulders 46, 47 formed interiorly on the cap at the juncture of the wall 41 with the wall 45. The shoulders 46, 47 are concentric and straight (as viewed in cross-section, FIG. 5), the outer shoulder 47 being off-set toward the open end of the cap and joined to the inner shoulder 46 by an inclined annular surface 48. The outer shoulder 47 is nearer the open end of the cap than inner shoulder 46 and both shoulders are inclined toward the open end.

Conversely, the edge 28 of receptacle inner wall 21 extends outwardly of the cavity 24 further than the edge 29 of the receptacle outer wall 23. Thus, when the receptacle 20 and cap 40 are joined and screwed together tightly, the seals of the ribs 26 and 27 with shoulders 46 and 47 are at axially off-set positions, providing two seals for the mercury. One seal, rib 26 against shoulder 46, prevents access of mercury into the chamber 22 and to the powder therein. The second seal, rib 27, against shoulder 47 prevents passage of mercury outwardly of the capsule. These seals ensure separation of the mercury and the silver alloy during shipment and storage and also prevents leakage during trituration.

The peaked shape of the ribs allows more deformation than, and better sealing than, ribs shaped otherwise.

To further ensure both separation of the mercury and the silver alloy powder and prevention of leakage, double seals are provided in each case. For that purpose, the uppermost exterior cylindrical surface 23x of the receptacle wall 23 above the screw thread 25 is designed to have a tight fit with the inner wall 49 of the enlarged mouth 44 of the cap, inwardly of the screw thread 45. This tight fit, together with the rib 27, provides an outer double seal to prevent leakage of the mercury outwardly during shipment and storage.

The second seal against access of the mercury to the chamber 22 and the powder therein is provided by abutment of the upper right edge of the wall 21 (see FIG. 6) against the inclined surface 48 (see FIG. 5) which connects the shoulders 46 and 47. This abutment occurs when the cap 40 is screwed tight on the container part 20. This double seal may be considered an inner double seal, in contrast to the outer double seal previously described.

Location of the above-mentioned seals in an area near the center of the capsule and away from the area of impact at the ends of the mixing chamber of the mercury, alloy and pestle 55 enhances the effectiveness of the seals during trituration. The receptacle preferably has a wide flange 30 extending radially outwardly from the wall 21 for gripping by the fingers of the operator during tightening and release of the receptacle and cap. The outer surface of the flange is preferably knurled or striated to prevent slippage of the operator's fingers.

Likewise, the exterior surface 50 of the enlarged wall portion 43 is knurled, striated or roughened.

The receptacle flange 30 is preferably cored out at 31 to omit unnecessary material and to impart some flexure, under finger pressure, to aid unscrewing. For like reasons, the cap is cored at 51 inwardly of the enlarged wall 43 above the sealing area.

If desired, to further assist the gripping and turning of the cap and receptacle, their roughened surfaces 32 and 50 may be hexagonal in shape as shown in FIG. 7.

The capsule is preferably made of synthetic molded plastic material which is non-reactive with the ingredients in connection with which it is to be used, e.g., mercury and silver alloy powders. One example of such material is natural polypropylene which may be colored or not.

In use the mercury and the powder are deposited separately in the cavity 24 and cavity 22, respectively, of the container part as viewed in FIG. 2. Then the cap 40 is screwed on the container, tightly, for storage and shipment. When the amalgam is to be prepared, the cap is partially unscrewed with the capsule inverted as shown in FIG. 4, so that the mercury and powder flow together. Then the cap and container parts are screwed tightly together, re-engaging the two double seals, in preparation for shaking the capsule and trituration of the ingredients.

While the invention is particularly useful in dentistry for the storage, transportation and mixing of mercury and silver alloy powders, it is not limited to such use but may as well be used with other solid or liquid ingredients or both.

Many modifications will occur to those skilled in the art. Therefore, the invention is not limited to the specific form and arrangement illustrated.

We claim:

1. A container for storing and mixing ingredients consisting of:
a first part having an inner, first wall and an outer, second wall, said first wall having a circumferential first wall edge on which first annular sealing means are formed, said first wall defining an inner cavity open at one end and adapted to hold a first ingredient, said second wall having a second wall edge on which second annular sealing means are formed, said second wall being disposed circumferentially outwardly of said first wall and joined thereto to define an annular cavity disposed outwardly of said first wall edge and open at one end, said annular cavity being adapted to hold a second ingredient, said open ends of said first and annular cavities facing in the same direction and said second sealing means being disposed concentrically outwardly of said first sealing means;
a second part having a second part wall defining a second cavity open at one end, said second part further having an annular shoulder means formed thereon;
respective cooperating interengageable means formed, respectively, on said first and second parts and adapted to cooperate with each other to engage said first and second parts with each other whereby said first and second cavities cooperate to form a mixing chamber and said first and second sealing means firmly engage said annular shoulder means to seal said annular cavity and said mixing chamber both from each other and from exteriorly of said container, said interengageable means being releasable by relative rotational movement of said first and second parts to a selected extent whereby said first and second parts are axially moved relative to each other to separate said first sealing means from said annular shoulder means sufficiently to provide a flow path over the entire periphery of said shoulder means from said annular cavity to said mixing chamber while maintaining both sealed from exteriorly of said container so that upon inverting of said container the second ingredient in said annular cavity may flow into said mixing chamber for mixing of said ingredients.

2. A container as claimed in claim 1 wherein said first and second sealing means are annular concentric ribs.

3. A container as claimed in claim 2 wherein said inter-engaging means are mating screw threads formed on said first and second parts.

4. A container as claimed in claim 2 in which said ribs are formed with substantially straight converging sides meeting at an approximately 90° angle.

5. A container as claimed in claim 1 wherein said inter-engaging means are mating screw threads formed, respectively, on said first and second parts.

6. A container as claimed in claim 1 further including an inclined portion on said second container part adjacent said annular shoulder means and positioned and configured to sealingly engage said first wall adjacent said first wall edge when said first and second parts are engaged by said interengageable means to provide a second inner seal which cooperates with said first sealing means to provide a double seal between said mixing chamber and said annular cavity.

7. A container as claimed in claim 6 further including a circumferentially extending surface on said first part adjacent said second wall edge thereof, said circumferentially extending surface being positioned and configured to sealingly engage said second part when said first and second parts are engaged by said interengageable means to provide a second outer seal which cooperates with said second sealing means to provide a double seal between said annular cavity and exteriorly of said container.

8. A container as claimed in claim 1 further including a circumferentially extending extending surface on said first part adjacent said second wall edge thereof, said circumferentially extending surface being positioned and configured to sealingly engage said second part when said first and second parts are engaged by said interengageable means to provide a second outer seal which cooperates with said second sealing means to provide a double seal between said annular cavity and exteriorly of said container.

9. A container for storing and mixing ingredients consisting of:
a first part having an inner, first wall and an outer, second wall, said first wall having a circumferential first wall edge on which a first annular sealing rib is formed, said first wall defining an inner cavity open at one end and adapted to hold a first ingredient, said second wall having exterior screw threads formed thereon and further having a second wall edge on which a second annular sealing rib is formed, said second wall being disposed circumferentially outwardly of said first wall and having a circumferentially extending surface on the exterior thereof disposed adjacent said second wall edge and adjacent one end of said exterior screw threads and concentrically therewith, said second wall being joined to said first wall to define therewith an annular cavity disposed outwardly of said first wall edge and open at one end, said annular cavity being adapted to hold a second ingredient, said open ends of said first and annular cavities facing in the same direction and said second sealing rib being disposed concentrically outwardly of said first sealing rib;
a second part having a second part wall having interior screw threads formed thereon, said second part wall defining a second cavity open at one end, said second part further having an annular shoulder means formed thereon interiorly of said second cavity and adjacent the interior end of said interior screw thread and concentrically therewith, and an annular inclined portion adjacent said annular shoulder and concentric therewith;
said interior and exterior screw threads being adapted to cooperate with each other to engage said first and second parts with each other whereby said first and second cavities cooperate to form a mixing chamber and said first and second sealing ribs firmly engage said annular shoulder means and said inclined portion firmly engages said first wall adjacent said first wall edge and said circumferentially extending surface firmly engages said second part, whereby to double seal said annular cavity and said mixing chamber both from each other and from exteriorly of said container, said interior and exterior screw threads being releasable by relative rotational movement of said first and second parts to a selected extent whereby said first and second parts are axially moved relative to each other to separate said first sealing means from said annular shoulder means and said inclined portion from said first wall sufficiently to provide a flow path over the entire periphery of said shoulder means from said annular cavity to said mixing chamber while maintaining both sealed from exteriorly of said container so that upon inverting of said container, the second ingredient in said annular cavity may flow into said mixing chamber for mixing of said ingredients.

* * * * *